United States Patent
Kirschner

(10) Patent No.: US 7,017,868 B2
(45) Date of Patent: Mar. 28, 2006

(54) FIRE SPRINKLER MOUNT

(75) Inventor: Kraig A. Kirschner, Corona, CA (US)

(73) Assignee: Automatic Fire Control Incorporated, South El Monte, CA (US)

( * ) Notice: Subject to any disclaimer, the term of this patent is extended or adjusted under 35 U.S.C. 154(b) by 0 days.

(21) Appl. No.: 10/670,127

(22) Filed: Sep. 24, 2003

(65) Prior Publication Data

US 2004/0117053 A1 Jun. 17, 2004

Related U.S. Application Data

(63) Continuation-in-part of application No. 09/616,723, filed on Jul. 14, 2000, now Pat. No. 6,594,539.

(60) Provisional application No. 60/178,695, filed on Jan. 28, 2000, provisional application No. 60/144,010, filed on Jul. 15, 1999.

(51) Int. Cl.
*A62C 13/76* (2006.01)
*B05B 15/06* (2006.01)

(52) U.S. Cl. ........................ 248/75; 248/327; 239/282; 239/283; 169/37

(58) Field of Classification Search .................. 248/75, 248/70, 327, 342, 343; 239/282, 283; 169/37
See application file for complete search history.

(56) References Cited

U.S. PATENT DOCUMENTS

| 3,653,104 A | * | 4/1972 | Nelson | 27/12 |
| 3,995,823 A | | 12/1976 | Hensel | 248/327 |
| 4,070,737 A | * | 1/1978 | Peterson | 27/12 |
| 4,346,863 A | | 8/1982 | Zeitrager et al. | 248/75 |
| 5,224,682 A | | 7/1993 | Baughnam | 248/651 |
| 5,829,718 A | * | 11/1998 | Smith | 248/55 |
| 6,508,410 B1 | | 1/2003 | Thomas et al. | 239/1 |

FOREIGN PATENT DOCUMENTS

| JP | 2-296949 | 12/1990 |
| JP | 2-363452 A | 12/1992 |

* cited by examiner

*Primary Examiner*—Anita M. King
(74) *Attorney, Agent, or Firm*—Fulbright & Jaworski L.L.P.

(57) ABSTRACT

A fire sprinkler mount including a base (26), a bracket (46) and a rod (60) mounting the bracket (46) to the base (26). The base (26) includes a body (28) attachable to a beam (10) with two arms (38, 40) extending therefrom. Support holes (42, 44) extend through the arms (38, 40). The bracket (46) includes a plate (48) with a retaining hole (58) to receive a standard sprinkler fitting (16, 20). The rod (60) is able to rotate within the support holes (42, 44) and is threaded to a mounting hole (56) in the bracket (46) for vertical adjustment of the bracket (46) retaining the sprinkler fitting (16, 20). The base (26) also includes a support having a body (28) and attachment wings (30, 32). The body (28) can be in a displaced parallel plane to that of the attachment wings (30, 32).

8 Claims, 2 Drawing Sheets

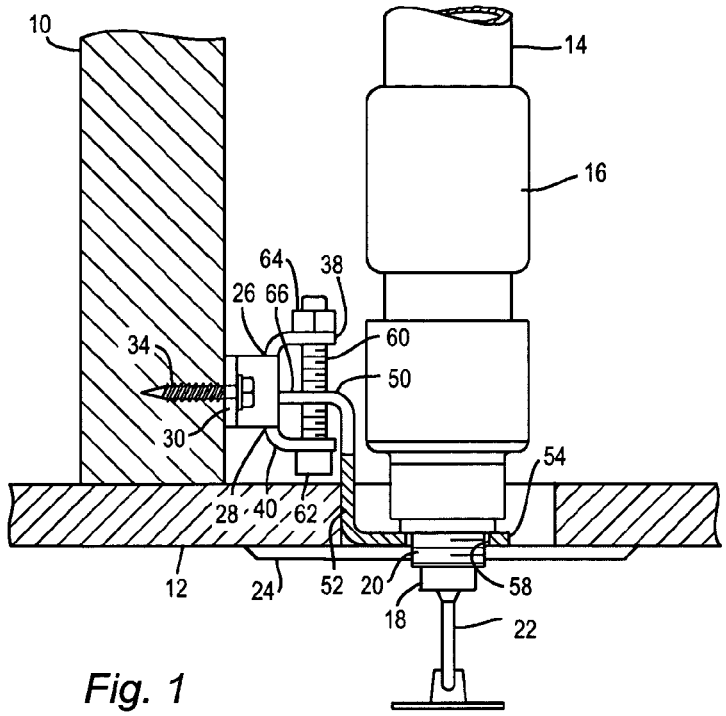
Fig. 1
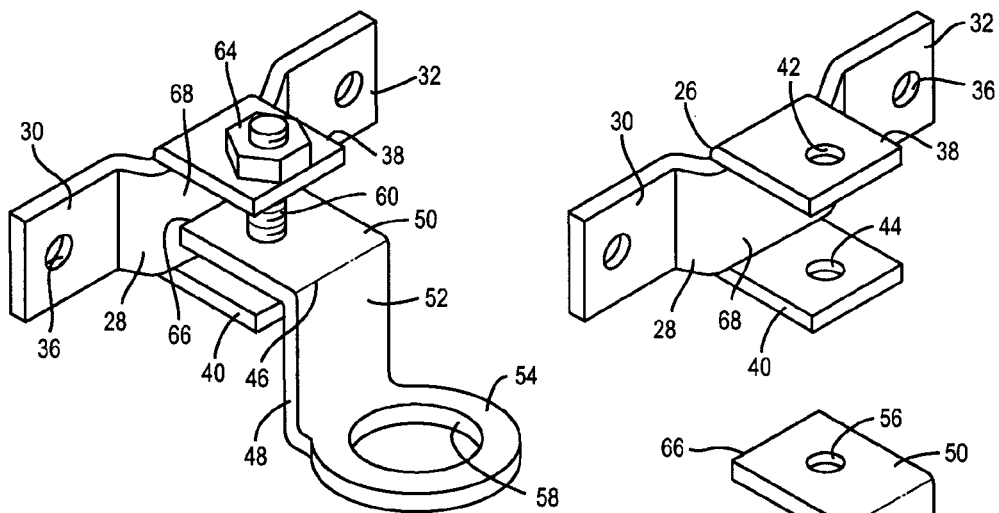
Fig. 2     Fig. 3
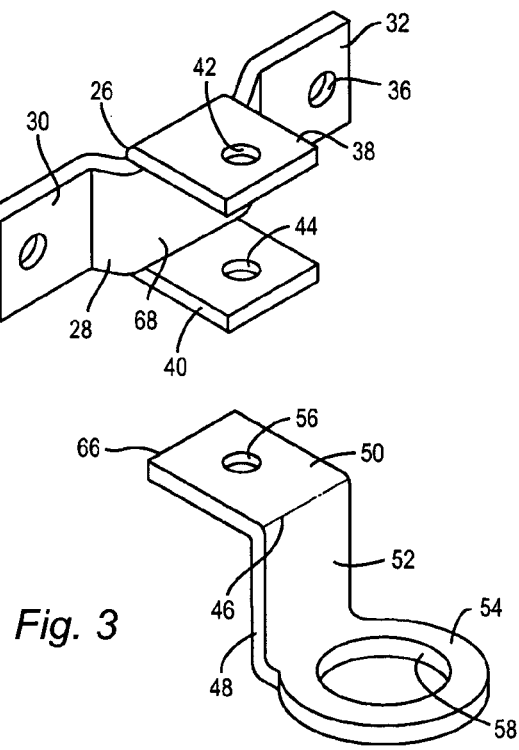

FIRE SPRINKLER MOUNT

This application is a continuation-in-part of application Ser. No. 09/616,723 filed Jul. 14, 2000, now U.S. Pat. No. 6,594,539, which claims domestic priority of provisional applications 60/144,010 filed Jul. 15, 1999 and 60/178,695 filed Jan. 28, 2000.

BACKGROUND OF THE INVENTION

The field of the present invention is mountings for fire sprinklers in buildings.

Fire sprinklers are commonly installed in buildings today. Safety regulations now require same in many applications. The sprinklers are most often installed in ceilings where the sprinkler head extends below the ceiling or is flush with the ceiling while the sprinkler fitting of which there are standard sizes is positioned in the space above the sprinkler head. The placement of the sprinkler head protruding or flush with the ceiling creates the need for locational adjustment. The adjustment may require displacement in the plane of the ceiling or vertically perpendicular to that plane.

In many applications, particularly in the home, the sprinkler system might include PVC pipe and fittings. Such components are typically glued together, requiring cutting and reassembling for adjustment. Further, the pipe is not as resistant to vibrational wear making it more easily damaged by metal fittings, clamps and the like. However, the piping tends to be more flexible than steel pipe or copper tubing. These attributes and detriments of PVC piping provide for reasonably easy locational adjustments but are less tolerant of being gripped and retained by conventional hardware.

SUMMARY OF THE INVENTION

The present invention is directed to an adjustable fire sprinkler mount which includes a base with a support having arms extending from the support and a support hole through each arm. A rod is associated with the base to adjustably mount a bracket which includes a plate including a retaining hole for engaging a fire sprinkler and a mounting hole. The rod extends through the mounting hole in the plate and the support holes of the base.

A first separate aspect of the present invention includes the support having a guide and the bracket having a follower cooperating with the guide to restrain the bracket from moving rotationally about the rod.

A second separate aspect of the present invention includes the retaining hole of the plate being displaced parallel to the direction of adjustment from the mounting of the bracket to the base.

A third separate aspect of the present invention includes the support having a body and attachment wings extending to either side of the body, the wings lying in a first plane and the body lying in a second plane parallel to and displaced from the first plane. Various distances from a support such as a beam to the sprinkler can be accommodated with only a change in the displacement between parallel planes.

As a further separate aspect, any of the foregoing separate aspects are contemplated to be employed in combination to further advantage.

Accordingly, it is an object of the present invention to provide an improved adjustable mount for fire sprinklers. Other and further objects and advantages will appear hereinafter.

BRIEF DESCRIPTION OF THE DRAWING

FIG. 1 is a side view of a fire sprinkler mount in place.
FIG. 2 is a perspective view of the fire sprinkler mount.
FIG. 3 is an exploded assembly perspective view of the base and bracket of the fire sprinkler mount.

DETAILED DESCRIPTION OF THE PREFERRED EMBODIMENTS

Figure 4:
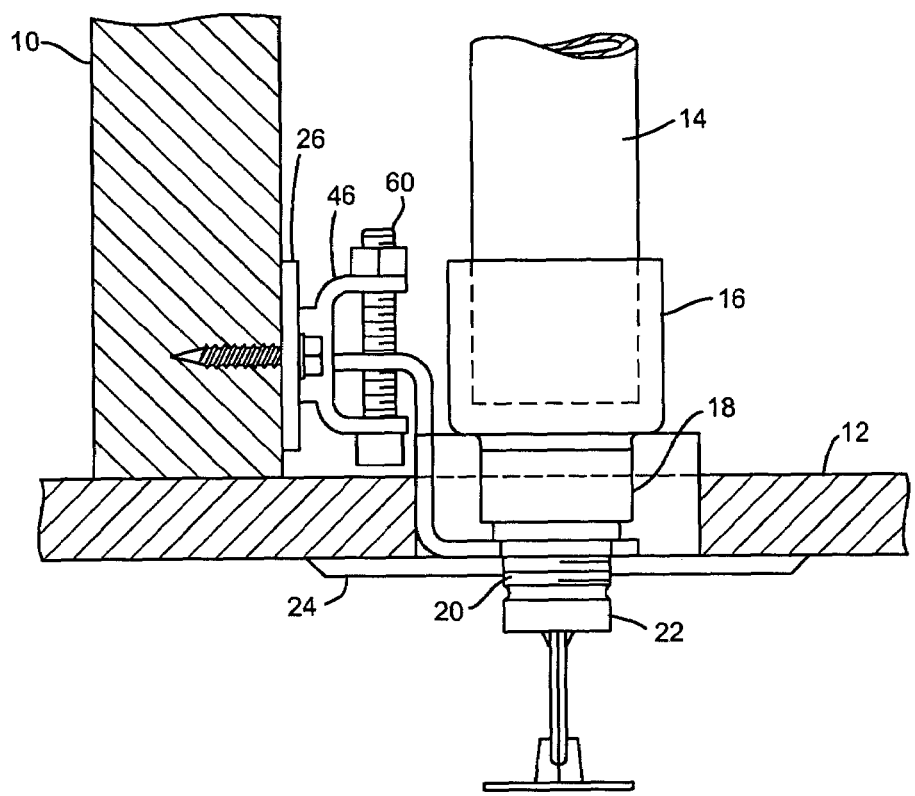
FIG. 4 is a side view of a fire sprinkler mount in place.

Turning in detail to the figures, a sprinkler mount is illustrated. The beam 10 lies immediately above a ceiling 12. A fire sprinkler pipe 14 extends downwardly from a sprinkler system raised above the ceiling 12. The pipe 14 terminates in a standard sprinkler fitting 16. This fitting 16 is, in this embodiment, two and one-half inches high. The pipe 14 and fitting 16 are typically PVC in residential construction and are permanently glued together. The fitting 16 is hollow with a threaded hole at the lower end thereof to receive a sprinkler head 18 to communicate water from the pipe 14 to the head 18 upon demand.

The sprinkler head 18 includes a threaded nipple 20 received in the threaded hole of the sprinkler fitting 16. The sprinkler head 18 includes a spray nozzle 22 which extends below the ceiling 12. A cover plate 24 finishes the hole through the ceiling 12.

The fire sprinkler mount includes a base 26 separately illustrated in FIG. 3. The base 26 is a formed plate with a support defined by a body 28 with attachment wings 30 and 32 extending to either side of the body 28. The wings 30 and 32 are to be placed in juxtaposition against the beam 10 for attachment by fasteners 34 through fastener holes 36. Above and below the body 28, an upper arm 38 and a lower arm 40 extend from the support. The upper arm 38 and the lower arm 40 extend mutually parallel to one another and are spaced apart by the body 28. The two arms 38 and 40 have aligned support holes 42 and 44, respectively. These holes 42, 44 are through holes which are not threaded. They are located toward the distal ends of the upper and lower arms 28 and 30 as can be discerned from the figures and define a mounting axis.

Figure 5:
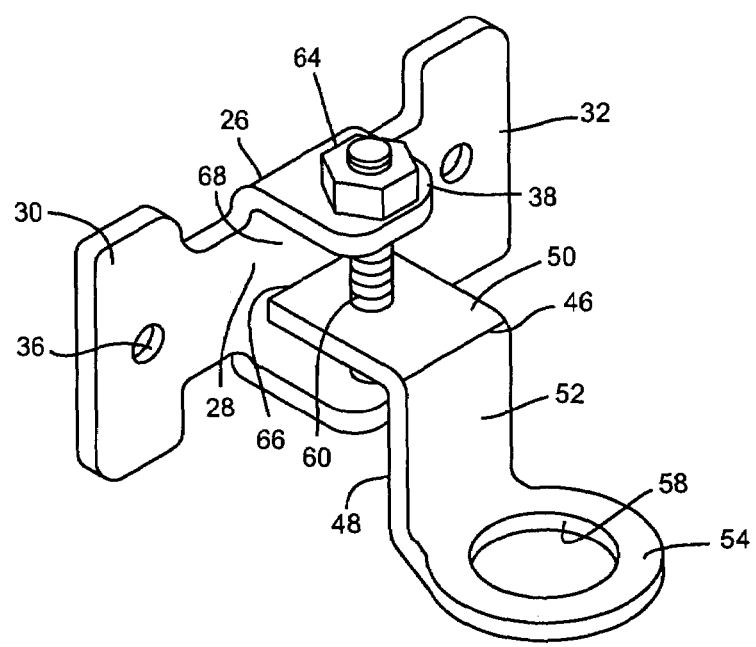
FIG. 5 is a perspective view of the fire sprinkler mount of FIG. 4.

The wings 30 and 32, in the version illustrated in FIGS. 1 through 3, are displaced in a parallel plane from the plane of the body 28. This displacement does not affect the distance from the base to the mounting axis defined by the aligned support holes 42 and 44. It does, however, increase the distance from the mounting plane of the wings 30 and 32 to the mounting axis. A universal standard has not been fully resolved for the distance from the beam surface to the centerline of the sprinkler. Through variation in the displacement of the wings 30 and 32, including no displacement as seen in the version illustrated in FIGS. 4 and 5, the same device with minimal and predefined alteration in the support for the base can accommodate a range of standards for the beam to centerline distance.

A bracket 46 is mounted to the base 26. The bracket 46 includes a formed plate 48. The plate 48 includes a mounting section 50, a vertical displacement section 52 and a retaining section 54. The mounting section 50 and the retaining section 54 are preferably parallel and displaced by the vertical dimension of the displacement section 52. A mounting hole 56 extends through the plate 48 in the mounting section 50. A retaining hole 58 extends through the plate 48 in the retaining section 54. The retaining hole 58 is sized to receive the threaded nipple 20 with a slip fit. The mounting hole 56 is threaded.

A rod 60 ties the base 28 together with the bracket 46 and provides vertical adjustment therebetween. The rod 60 is illustrated to be a machine screw passing through the support holes 42 and 44 in the two arms 38 and 40 and the mounting hole 56 in the plate 48 therebetween. The rod 60 is threaded to the mounting hole 56 which is tapped. The rod 60 defines shoulders at the rod ends thereof by an integral head 62 and a nut 64 at the ends of the threaded rod 60. The nut 64 may be a jamb nut or use other conventional techniques for allowing substantial rotation of the rod 60 without loosening or tightening the nut 64. The rod 60 is oriented with the integral head 62 at the bottom in order that a screwdriver or wrench may be applied through the ceiling for adjustment with removal of the cover plate 24.

Assembled, the edge of the mounting section 50 provides a follower 66 which approaches a guide 68 defined by the surface of the body 28 facing the rod 60. The follower 66 and guide 68 provide indexing for the bracket 46 relative to the base 26. The mount may hold the sprinkler head 18 under lateral force to keep the sprinkler head 18 and the cover plate 24 aligned properly with the ceiling. The bracket 46 provides displacement parallel to the alignment of the support holes 42 and 44 from its mounting section 50 to the retaining section 54 through the vertical displacement section 52. This allows for adequate adjustment and yet the base 26 remains displaced from the ceiling 12. At the same time the rod 60 remains laterally adjacent the sprinkler head 18 for vertical adjustment through the hole in the ceiling 12.

In operation, the base 26 is mounted to the beam 10 in the location where the mount can appropriately place the sprinkler head 18 relative to the ceiling 12. The mount is either preassembled or is assembled with the base 26 in place. The fire sprinkler pipe 14 is typically flexible and the fitting 16 is positioned within the mount. The threaded nipple 20 of the sprinkler head 18 is extended through the retaining hole 58 and threaded into the fitting 16. The rod 60 is then rotated to vertically adjust the height of the sprinkler head 18 such that the cover plate 24 when positioned on the sprinkler head 18 is flush with the ceiling 12. The head 62 of the rod 60 is laterally close to the retaining hole 58 so that adjustment access is through the hole in the ceiling to be covered by the cover plate 24. The mount provides for a remodeling of the ceiling to define a new lower surface thereof by further adjustment to the vertical location of the bracket 46. Adjusting the mount with this embodiment does not change the location of the screw head 62.

Accordingly, an improved fire sprinkler mount is disclosed. While embodiments and applications of this invention have been shown and described, it would be apparent to those skilled in the art that many more modifications are possible without departing from the inventive concepts herein. The invention, therefore is not to be restricted except in the spirit of the appended claims.

What is claimed is:

1. A mount for a fire sprinkler comprising
a base including a support, a first arm extending from the support, a second arm extending from the support and displaced from the first arm and a guide, the first arm having a first support hole through the first arm and the second arm having a second support hole through the second arm and aligned with the first support hole;
a bracket including a first end, a second end, a retaining hole adjacent the first end to receive the fire sprinkler, a mounting hole adjacent the second end and a follower engaging the guide, the first end extending from the second end away from the base;
a threaded rod extending through the first support hole, the second support hole and the mounting hole and adjustably mounting the bracket parallel with the alignment of the first and second support holes and restraining the bracket from moving laterally of the alignment of the first and second support holes, the engagement of the guide and the follower restraining the bracket from moving rotationally about the rod, the guide being a surface on the support, facing and parallel to the threaded rod, the follower being the end surface on the second end.

2. The mount of claim 1, the mounting hole being threaded on the threaded rod, the threaded rod including rod ends with shoulders not extendable through the first and second support holes.

3. The mount of claim 2, one of the rod ends having a nut thereon defining one of the shoulders and the other of the rod ends having an integral head defining the other of the shoulders.

4. The mount of claim 1, the first arm and the second arm being parallel to one another at the first support hole and the second support hole.

5. The mount of claim 2, the first arm and the second arm being parallel.

6. The mount of claim 1, the support having a body and attachment wings extending to either side of the body and lying in a first plane, the body lying in a second plane parallel to and displaced from the first plane.

7. A mount for a fire sprinkler comprising
a base including a support, a first arm extending from the support, a second arm extending from the support displaced from the first arm and a guide, the first arm having a first support hole through the first arm and the second arm having a second support hole through the second arm and aligned with the first hole, the guide being parallel with the alignment between the first and second holes;
a bracket including a first end, a second end, a retaining hole adjacent the first end to receive the fire sprinkler, a mounting hole adjacent the second end and between the first and second arms, and a follower engaging the guide, the retaining hole being displaced in the direction of the alignment of the first and second support holes from the mounting hole to beyond the second arm and extending from the second end away from the base;
a threaded rod extending through the first support hole, the second support hole and the first mounting hole adjustably mounting the bracket parallel with the alignment and restraining the bracket from moving laterally of the alignment, the guide and follower engagement restraining the bracket from moving rotationally about the rod, the mounting hole being threaded on the threaded rod, the guide being a surface on the support, facing and parallel to the threaded rod, the follower being the end surface on the second end.

8. The mount of claim 7, the support having a body and attachment wings extending to either side of the body and lying in a first plane, the body lying in a second plane parallel to and displaced from the first plane.

* * * * *